United States Patent
Del Rio et al.

(10) Patent No.: US 6,607,533 B2
(45) Date of Patent: Aug. 19, 2003

(54) MINIATURE CUTTER SHAFT CONFIGURATION

(75) Inventors: Eddy Del Rio, Royal Palm Beach, FL (US); Jose M. Lamanna, Jupiter, FL (US); Douglas A. Perry, Palm Beach Gardens, FL (US); Thomas E. Anspach, Jupiter, FL (US)

(73) Assignee: The Anspbell Effort, Inc, Palm Beach Gardens, FL (US)

( * ) Notice: Subject to any disclaimer, the term of this patent is extended or adjusted under 35 U.S.C. 154(b) by 157 days.

(21) Appl. No.: 09/962,461

(22) Filed: Sep. 25, 2001

(65) Prior Publication Data

US 2003/0060829 A1 Mar. 27, 2003

(51) Int. Cl.[7] ............................................. A61B 17/00
(52) U.S. Cl. ......................................... 606/80; 408/226
(58) Field of Search .............................. 606/79, 80, 81, 606/87, 65, 67, 96; 433/165, 166, 127, 128; 408/226

(56) References Cited

U.S. PATENT DOCUMENTS

| | | | | |
|---|---|---|---|---|
| 4,255,145 A | * | 3/1981 | Weissman | .................. 433/165 |
| 4,850,758 A | * | 7/1989 | Morgan | ..................... 408/226 |
| 5,632,620 A | * | 5/1997 | Musikant et al. | ........... 433/102 |
| 5,634,933 A | * | 6/1997 | McCombs et al. | .......... 606/180 |
| 5,741,267 A | * | 4/1998 | Jorneus et al. | .............. 606/102 |
| 5,785,522 A | * | 7/1998 | Bergstrom et al. | ............ 433/72 |
| 6,227,854 B1 | * | 5/2001 | Helfenbein et al. | ......... 433/128 |

* cited by examiner

Primary Examiner—Eduardo C. Robert
(74) Attorney, Agent, or Firm—Norman Friedland

(57) ABSTRACT

A cutter for a surgical drill and/or attachment includes a configured groove section at the proximal end that fits into a clutch mechanism in the drill or attachment. The distal end portion is flattened at above the center line and extends axially a short distance and defines a shoulder with the outer circumference of the shaft of the cutter. A pair of diametrically grooves disposed downstream of the shoulder toward the distal end are formed on the upper and lower portion of the shaft and are oriented in a horizontal plane passing through the center of the flat portion and include in each of the grooves a pair of predetermined angular grooves displaced from the upper circumferential surface with the apex of the angle being in the horizontal plane and another groove adjacent to and upstream of the shoulder toward the proximate end with a predetermined angle with the apex passing through the horizontal plane.

12 Claims, 2 Drawing Sheets

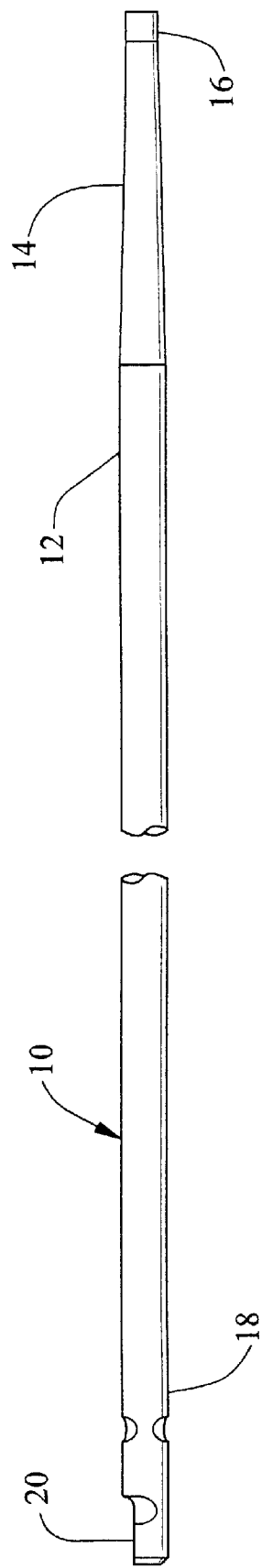
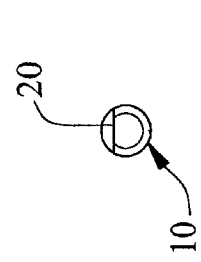
*FIG. 1*
*FIG. 2*

MINIATURE CUTTER SHAFT CONFIGURATION

TECHNICAL FIELD

This invention relates to cutters or tool bits used for surgical procedures and more particularly for cutters or tool bits that include mechanism for coupling the cutters tool bit to the surgical drill and/or attachment driven by a surgical drill.

CROSS REFERENCES

The following patent applications, contemporaneously filed with this patent application and assigned to the same assignee, relate to the subject matter of this patent application and are incorporated herein by reference. They include the patent application entitled "Bearings for Surgical Instruments" filed by Eddy H. Del Rio, Jose M. Lamanna, Douglas A. Perry and Thomas D. Anspach (Attorney Docket No. N880) and the patent application entitled "Miniature Clutch for High Speed Surgical Drills" filed by Eddy H. Del Rio, Douglas A. Perry, Jose M. Lamanna and Thomas D. Anspach (Attorney Docket No. N878).

BACKGROUND OF THE INVENTION

The surgical drill typically accommodates sundry tool bits such as cutting burrs, saw blades, etc, (cutters) and different sizes thereof and during a surgical procedure different tool bits may be required. It is therefore necessary for the surgical drill or attachment to provide means for coupling the tool bit easily and timely with a minimum of time required to remove the incumbent tool bit and replace it with a new one.

This invention constitutes an improvement on surgical rotary cutters by incorporating a unique design at the proximate end of the shaft of the cutter so as to be capable of utilizing a clutching mechanism in the surgical drill or attachment and being characterized as simple to assemble and disassemble, requiring minimum amount of time for performing these function, while having the ability to be reliably secured in the clutch mechanism. In accordance with this invention the tool bit is inserted in the surgical drill or attachment to a point beyond where the operator feels a slight force exerted by a latching spring and slightly rotates the tool bit to its locked position. The operator, of course, has no limitations as to when the rotation of the tool bit starts when inserted into the attachment and/or drill, except at the end of the travel. The removal is merely by turning and pulling on the tool bit simultaneously in the direction for removal from the drill or attachment. We have found that the assembly and disassembly, with a minimum of experimental time or learning time to obtain the requisite skill, the procedure is almost instantaneous. The rotating mechanism of the drill and/or attachment needs to be held stationary during this procedure.

U.S. Pat. No. 5,405,348 granted on Apr. 11, 1995 to William E. Anspach, Jr. and Eddy H. Del Rio, the joint inventor of the present application, and entitled "Surgical Cutting Instrument" exemplifies the cutters to which this invention pertains. In this patent It will be appreciated that the proximate end of the cutter fits into jaws of a clutch that is activated mechanically by positioning the jaws radially inward to bear against the outer surface of the cutter shaft to secure it in place during the drilling procedure and the jaws are retracted to release the cutter. Obviously, in the heretofore known mechanism of the type known and that being described herein, this procedure or similar procedure for assembly and disassembly of the cutter is not only cumbersome but is also time consuming. This invention constitutes an improvement of this type of mechanism by incorporating in the end of the cutter a unique attachment design for automatically being retained by a clutching mechanism which is characterized by avoiding the typical manually operated clutching mechanism.

SUMMARY OF THE INVENTION

An object of this invention is to provide an improved cutter design for surgical drill wherein the proximal end is configured to be easily assembled and disassembled in an automatic clutch mechanism.

A feature of this invention is that the proximal end of the shaft of the cutter is milled or cut axially to define a flat portion and an adjacent shoulder, and a pair of angularly disposed grooves relative to a plane extending centrally of said flat portion and extending radially through the shaft at the shoulder within the flat portion and extending radially toward the center line of the shank and another pair of grooves axially spaced from said pair of angularly disposed grooves and each of said other grooves having a given angular dimension and a given relationship to the first pair of grooves. The back surfaces relative to the proximal end of the grooves bear a predetermined parallel relationship and one of the grooves axially spaced from the groove in the flat portion is in-line therewith and the second groove axially spaced from said groove in the flat portion is diametrically disposed with that one groove.

A cutter with a shaft having a given cut out at the proximate end to accommodate a clutch mechanism is characterized as relatively simple to fabricate, relatively inexpensive, easy to install in the clutch mechanism and to remove therefrom, is reliable to rotate with the drill motor and is rotatable in a clockwise and counterclockwise direction.

The foregoing and other features of the present invention will become more apparent from the following description and accompanying drawings.

BRIEF DESCRIPTION OF THE DRAWINGS

FIG. 1 is a side view in elevation illustrating a cutter incorporating this invention;

FIG. 2 is a plan view of the proximal end of the cutter depicted in FIG. 1;

Figure 3:
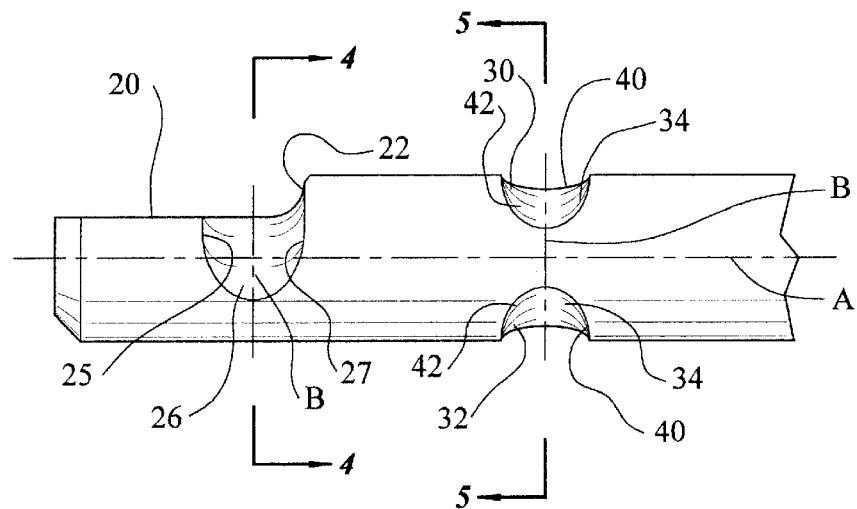
FIG. 3 is an enlarged view of the proximal end of the cutter depicted in FIG. 1.

These figures merely serve to further clarify and illustrate the present invention and are not intended to limit the scope thereof

DETAILED DESCRIPTION OF THE INVENTION

As is obvious to one skilled in this technology, the cutter described herein is merely exemplary of cutters of this type and is being described to disclose the preferred embodiment. It should be understood that there are a multitude of cutters that can utilize this invention and the scope of the invention should not be limited because of the specific cutter being described.

Reference should be made to all the Figures which show the cutter generally illustrated as reference numeral 10 having an elongated cylindrical shaft 12 that may be tapered at the distal end 14 and carries a cutting burr 16 and is judiciously configured at the proximal end 18 with a cut-out section which is designed to be coupled to a clutch mechanism carried by the surgical drill motor assembly or in an attachment that is typically attached to the surgical drill motor to meet certain specifications for performing surgical procedures, as for example, transoral, transphemoidal and similar restricted access approaches. As mentioned in the hereinabove paragraphs, the cutters utilized with these types of bits are well known and the invention pertains only to the proximate end that is uniquely designed for automatic clutching to be retained in the surgical drill or its attachment.

Figure 4:
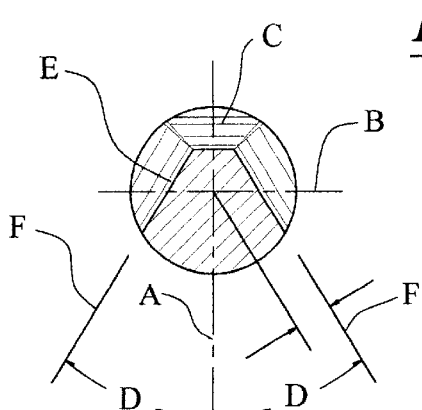
FIG. 4. is a sectional view taken along the section lines 4—4 of FIG. 3.

The end of the proximal end portion 18 is milled or flattened to form a planar portion 20 extending partly axially inward toward the distal end to define the shoulder 22. Adjacent the shoulder 22 and in the planar portion 20 a pair of diametrically opposed grooves 24 and 26 are cut into the shaft 12 and each defining a truncated triangle E with the removed extended apex C forming angle D substantially equal to a 30 degree (°) angle with respect to a plane A extending centrally of the transverse (vertical) axis bisecting the plane B extending centrally of the axial (horizontal) axis and perpendicular therewith. It will be appreciated from FIG. 4 that the apex C lies in coincidence with the top surface of the planar portion 20. Hence, the groove begins from the flat and has a front wall 25 toward the proximal end 18 of the shaft 12 and a rear wall 27 toward the distal end 14 of shaft 12.

Figure 5:
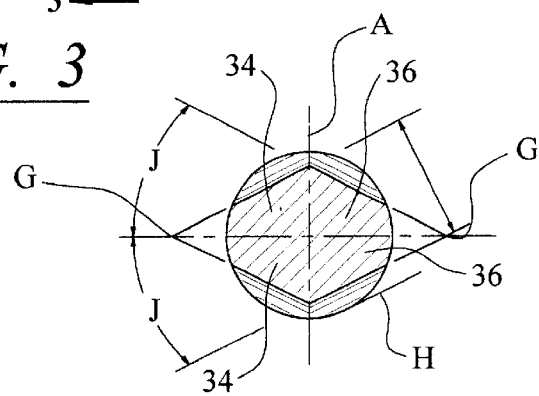
FIG. 5 is a sectional view taken along the lines 5—5 of FIG. 3.
Figure 6:
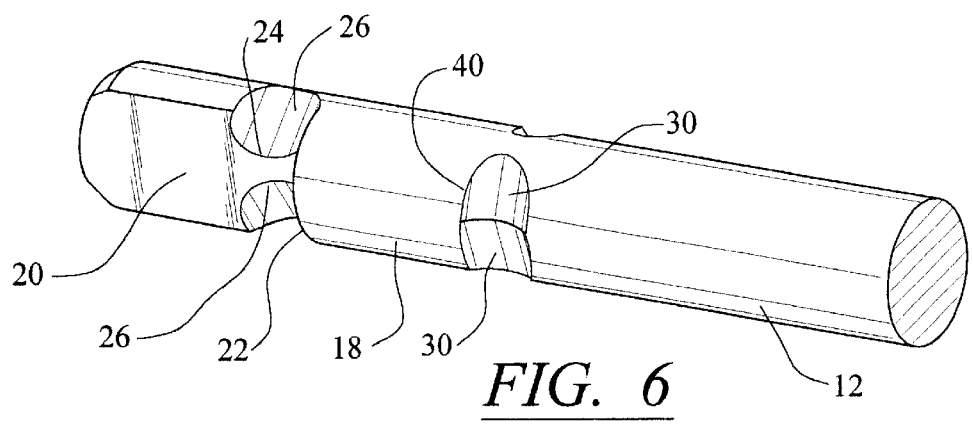
FIG. 6 is a perspective view of the proximal end of the cutter shaft and illustrates the details of this invention.

Spaced a short axial distance from shoulder 22 and toward the distal end 14 of shaft 12, are a pair of groove configurations 30 and 32 diametrically opposed to each other and each groove configurations 30 and 32 includes a groove 34 having an extended apex G lying in coincidence with the plane B and a diametrically opposed groove 36 lying in coincidence with plane B and also having an extended apex G each defining a triangle with an angle J being substantially equal to 25°. As will be noted from FIG. 5 the grooves 34 and 36 start just below the outer circumference of the shaft 12, say at substantially 0.010 inch and the intersection of the base H which is in coincidence with the plane A. As is apparent from the foregoing the groove configurations 30 and 32 are configured identical to each other and when installed in the clutch mechanism of the surgical drill or its attachment, the groove configurations allow the drill bit to be rotated either clockwise or counterclockwise directions. Each of the grooves 34 and 36 have a back wall 40 facing the proximate end 14 of shaft 12 and a forward wall 42 facing the distal end 18 of shaft 12. The back wall 27 and the back wall 40 are parallel to each other.

Although this invention has been shown and described with respect to detailed embodiments thereof, it will be appreciated and understood by those skilled in the art that various changes in form and detail thereof may be made without departing from the spirit and scope of the claimed invention.

We claim:

1. A cutter for use in a surgical instrument having a proximate end and a distal end, said cutter having a shank portion, a cutting surface at the distal end, and a cut-out configuration portion adapted to be locked in a surgical drill or an adapter for the surgical drill at the proximate end, said cutter being circular in cross section, a milled out portion defining a flat surface formed on the distal end extending a short distance toward the proximate end, a first pair of opposing radially extending grooves adjacent to said flat portion and a second pair of radially extending grooves axially spaced from said first pair of radially extending grooves.

2. A cutter for use in a surgical instrument having a proximate end and a distal end as claimed in claim 1 including a shoulder formed adjacent to the end portion of said flat portion remote from said proximate end.

3. A cutter for use in a surgical instrument having a proximate end and a distal end as claimed in claim 2 wherein said first pair of radially extending grooves including one of said pair of radially extending grooves having a groove dimension that forms substantially a 30 degree angle relative to a plane extending transversely through the center of said shank and the other of groove of said pair of grooves having a groove dimension that forms substantially a 30 degree angle relative to a plane extending transversely through the center of said shank and each of said grooves of said pair of radially extending grooves being on opposite sides of said shank and having a common apex.

4. A cutter for use in a surgical instrument having a proximate end and a distal end as claimed in claim 3 wherein said second pair of radially extending grooves includes a first groove of said pair of radially extending grooves having a groove dimension that forms substantially a 25 degree angle relative to a plane extending transversely through the center of said shank and a second groove having a groove dimension that forms substantially a 25 degree angle relative to a plane extending transversely through the center of said shank and having an apex common to the apex of said first groove.

5. A cutter for use in a surgical instrument having a proximate end and a distal as claimed in claim 4 wherein said apex of said second pair of grooves is below the outer surface of said shank.

6. A cutter for use in a surgical instrument having a proximate end and a distal as claimed in claim 5 wherein said shank includes a third pair of grooves diametrically opposed to said second pair of grooves.

7. A cutter for use in a surgical instrument having a proximate end and a distal as claimed in claim 6 wherein said third pair of radially extending grooves includes a first groove of said pair of radially extending grooves having a groove dimension that forms substantially a 25 degree angle relative to a plane extending transversely through the center of said shank and a second groove having a groove dimension that forms substantially a 25 degree angle relative to a plane extending transversely through the center of said shank and having an apex common to the apex of said first groove.

8. A cutter for use in a surgical instrument having a proximate end and a distal end as claimed in claim 7 wherein said apex of said second pair of grooves is below the outer surface of said shank.

9. A cutter for use in a surgical instrument having a proximate end and a distal end said cutter having a shank portion, a cutting surface at the distal end, and a cut-out configuration portion adapted to be locked in a surgical drill or an adapter for the surgical drill at the proximate end, said cutter being circular in cross section, a milled out portion defining a flat surface formed on the distal end extending a short distance toward the proximate end, a first pair of opposing radially extending grooves adjacent to said flat portion and a second pair of radially extending grooves axially spaced from said first pair of radially extending grooves, a shoulder formed adjacent to the end portion of said flat portion remote from said proximate end, said first pair of radially extending grooves including one of said pair of radially extending grooves having a groove dimension that forms substantially a 30 degree angle relative to a plane extending transversely through the center of said shank and the other of groove of said pair of grooves having a groove dimension that forms substantially a 30 degree angle relative to a plane extending transversely through the center of said shank and each of said grooves of said pair of radially extending grooves being on opposite sides of said shank and having a common apex, said second pair of radially extending grooves includes a first groove of said pair of radially extending grooves having a groove dimension that forms substantially a 25 degree angle relative to a plane extending transversely through the center of said shank and a second groove having a groove dimension that forms substantially a 25 degree angle relative to a plane extending transversely through the center of said shank and having an apex common to the apex of said first groove.

10. A cutter for use in a surgical instrument having a proximate end and a distal end as claimed in claim 9 wherein said apex of said second pair of grooves is below the outer surface of said shank.

11. A cutter for use in a surgical instrument having a proximate end and a distal end said cutter having a shank portion, a cutting surface at the distal end, and a cut-out configuration portion adapted to be locked in a surgical drill or an adapter for the surgical drill at the proximate end, said cutter being circular in cross section, a milled out portion defining a flat surface formed on the distal end extending a short distance toward the proximate end, a first pair of opposing radially extending grooves adjacent to said flat portion and a second pair of radially extending grooves axially spaced from said first pair of radially extending grooves, a shoulder formed adjacent to the end portion of said flat portion remote from said proximate end, said first pair of radially extending grooves including one of said pair of radially extending grooves having a groove dimension that forms substantially a 30 degree angle relative to a plane extending transversely through the center of said shank and the other of groove of said pair of grooves having a groove dimension that forms substantially a 30 degree angle relative to a plane extending transversely through the center of said shank and each of said grooves of said pair of radially extending grooves being on opposite sides of said shank and having a common apex, said second pair of radially extending grooves includes a first groove of said pair of radially extending grooves having a groove dimension that forms substantially a 25 degree angle relative to a plane extending transversely through the center of said shank and a second groove having a groove dimension that forms substantially a 25 degree angle relative to a plane extending transversely through the center of said shank and having an apex common to the apex of said first groove, said shank includes a third pair of grooves diametrically opposed to said second pair of grooves and said third pair of radially extending grooves includes a first groove of said pair of radially extending grooves having a groove dimension that forms substantially a 25 degree angle relative to a plane extending transversely through the center of said shank and a second groove having a groove dimension that forms substantially a 25 degree angle relative to a plane extending transversely through the center of said shank and having an apex common to the apex of said first groove.

12. A cutter for use in a surgical instrument having a proximate end and a distal end as claimed in claim 11 wherein said apex of said second pair of grooves is below the outer surface of said shank.

* * * * *